United States Patent
Long et al.

(10) Patent No.: US 12,037,560 B2
(45) Date of Patent: Jul. 16, 2024

(54) UV CURE TOPCOATINGS FOR MEDICAL DEVICES

(71) Applicant: Biocoat, Incorporated, Horsham, PA (US)

(72) Inventors: Tyler Richard Long, Royersford, PA (US); Casmir S. Ilenda, Southampton, PA (US)

(73) Assignee: Biocoat, Incorporated, Horsham, PA (US)

( * ) Notice: Subject to any disclaimer, the term of this patent is extended or adjusted under 35 U.S.C. 154(b) by 194 days.

(21) Appl. No.: 17/075,965

(22) Filed: Oct. 21, 2020

(65) Prior Publication Data

US 2021/0115350 A1    Apr. 22, 2021

Related U.S. Application Data

(60) Provisional application No. 62/923,722, filed on Oct. 21, 2019.

(51) Int. Cl.
| | |
|---|---|
| *C10M 107/42* | (2006.01) |
| *A61L 2/08* | (2006.01) |
| *A61L 2/20* | (2006.01) |
| *A61L 101/44* | (2006.01) |
| *C10N 40/00* | (2006.01) |
| *C10N 50/08* | (2006.01) |

(52) U.S. Cl.
CPC ........... *C10M 107/42* (2013.01); *A61L 2/081* (2013.01); *A61L 2/087* (2013.01); *A61L 2/206* (2013.01); *A61L 2101/44* (2020.08); *A61L 2202/21* (2013.01); *C10M 2217/0245* (2013.01); *C10N 2040/50* (2020.05); *C10N 2050/08* (2013.01)

(58) Field of Classification Search
CPC ......... C10M 107/42; C10M 2217/0245; A61L 2/081; A61L 2/087; A61L 2/206; A61L 2101/44; A61L 2202/21; C10N 2040/50; C10N 2050/08; C09D 133/26
See application file for complete search history.

(56) References Cited

U.S. PATENT DOCUMENTS

| | | |
|---|---|---|
| 2,999,056 A | 9/1961 | David |
| 4,349,467 A | 9/1982 | Williams et al. |
| 4,642,267 A | 2/1987 | Creasy et al. |
| 4,801,475 A | 1/1989 | Halpern et al. |
| 4,990,357 A | 2/1991 | Karakelle et al. |
| 5,002,582 A | 3/1991 | Guire et al. |
| 5,023,114 A | 6/1991 | Halpern et al. |
| 5,037,677 A | 8/1991 | Halpern et al. |
| 5,091,205 A | 2/1992 | Fan |
| 5,217,492 A | 6/1993 | Guire et al. |
| 5,443,455 A | 8/1995 | Hergenrother et al. |
| 5,509,899 A | 4/1996 | Fan et al. |
| 5,531,715 A | 7/1996 | Engelson et al. |
| 5,702,754 A | 12/1997 | Zhong |
| 5,749,837 A | 5/1998 | Palermo et al. |
| 5,789,018 A | 8/1998 | Engelson et al. |
| 6,048,620 A | 4/2000 | Zhong |
| 6,087,416 A | 7/2000 | Pearlstine et al. |
| 6,221,061 B1 | 4/2001 | Engelson et al. |
| 6,278,018 B1 | 8/2001 | Swan |
| 6,534,559 B1 | 3/2003 | Vanderlaan et al. |
| 6,558,798 B2 | 5/2003 | Zhong et al. |
| 6,673,453 B2 | 1/2004 | Beavers et al. |
| 6,709,706 B2 | 3/2004 | Zhong et al. |
| 7,384,984 B2 | 6/2008 | Lewandowski |
| 7,550,444 B2 | 6/2009 | Stucke et al. |
| 8,163,327 B2 | 4/2012 | Finley |
| 8,318,263 B2 | 11/2012 | Carlson et al. |
| 8,541,498 B2 | 9/2013 | Sandhu et al. |
| 9,375,517 B2 | 6/2016 | Babcock |
| 9,737,639 B2 | 8/2017 | Babcock |
| 10,525,170 B2 | 1/2020 | Havenstrite et al. |
| 11,441,092 B2 | 9/2022 | Rhodes et al. |
| 11,634,656 B2 | 4/2023 | Zhu et al. |
| 2002/0037984 A1 | 3/2002 | Vanderbilt |
| 2002/0041899 A1* | 4/2002 | Chudzik ................. A61L 31/16 424/487 |

(Continued)

FOREIGN PATENT DOCUMENTS

| | | |
|---|---|---|
| CN | 1889982 A | 1/2007 |
| CN | 1950116 A | 4/2007 |

(Continued)

OTHER PUBLICATIONS

Frech et al., "A Simple Noninvasive Technique to Test Nonthrombogenic Surfaces," The American Journal of Roentgenology, vol. 113 (1971), p. 765-768.

Ovitt et al., "Guidewire Thrombogenicity and Its Reduction", Radiology, vol. 111 (1974), p. 43-46.

Albarghouthi et al., "Poly-N-hydroxyethylacrylamide (polyDuramide ): A novel, hydrophilic, self-coating polymer matrix for DNA sequencing by capillary electrophoresis", Electrophoresis, vol. 23 (2002), p. 1429-1440.

Primary Examiner — Taiwo Oladapo

(74) Attorney, Agent, or Firm — BakerHostetler

(57) ABSTRACT

The invention concerns coating compositions for medical devices or medical implants comprising a polymer which is soluble in water or water-alcohol solutions, the polymer made from monomers comprising: (a) at least one monomer that is a photo radical generator, and (b) at least one monomer comprising one or both of (i) ethylenic monomers comprising at least one acidic group and (ii) one or more of acrylates or acrylamides; wherein the molar ratio of one or both of (i) ethylenic monomers comprising at least one acidic group and (ii) one or more of acrylates or acrylamides to photo radical generator group is 20:1 to 500:1.

19 Claims, No Drawings

(56) References Cited

U.S. PATENT DOCUMENTS

| | | | |
|---|---|---|---|
| 2007/0032882 A1 | 2/2007 | Lodhi et al. | |
| 2007/0141365 A1 | 6/2007 | Jelle et al. | |
| 2007/0286959 A1 | 12/2007 | Palmer | |
| 2008/0206096 A1 | 8/2008 | Deka | |
| 2008/0213334 A1 | 9/2008 | Lockwood et al. | |
| 2010/0247599 A1 | 9/2010 | Kroehen et al. | |
| 2011/0063567 A1 | 3/2011 | Domschke | |
| 2011/0200828 A1 | 8/2011 | Li et al. | |
| 2011/0134387 A1 | 9/2011 | Samuel et al. | |
| 2012/0178872 A1 | 7/2012 | Blanquer et al. | |
| 2013/0323291 A1* | 12/2013 | Li | A61L 31/14 524/502 |
| 2014/0004170 A1 | 1/2014 | Kroehen et al. | |
| 2014/0193474 A1 | 7/2014 | Babcock et al. | |
| 2017/0281831 A1 | 10/2017 | Militello | |
| 2018/0244927 A1 | 8/2018 | Mccoy et al. | |

FOREIGN PATENT DOCUMENTS

| | | | |
|---|---|---|---|
| CN | 107206119 A | 9/2017 | |
| CN | 108603136 A | 9/2018 | |
| CN | 109966560 A | 7/2019 | |
| EP | 0220919 A2 | 5/1987 | |
| EP | 0379156 A2 | 7/1990 | |
| EP | 0480809 A2 | 4/1992 | |
| EP | 0669837 A1 | 9/1995 | |
| EP | 0728487 A1 | 8/1996 | |
| EP | 0790839 A1 | 8/1997 | |
| EP | 0963761 A1 | 12/1999 | |
| JP | 2004520088 A * | 7/2004 | |
| JP | 2006176934 A | 7/2006 | |
| JP | 2010090049 A | 4/2010 | |
| JP | 2010126482 A | 6/2010 | |
| JP | 2011046619 A | 3/2011 | |
| JP | 2011046652 A | 3/2011 | |
| TW | 1287564 B | 10/2007 | |
| WO | 9614885 A1 | 5/1996 | |
| WO | 0078884 A1 | 12/2000 | |
| WO | 2010041527 A | 4/2010 | |
| WO | 2010/129328 A2 | 11/2010 | |
| WO | 2011125713 A1 | 3/2011 | |
| WO | 2010041530 A1 | 3/2012 | |
| WO | 2013/109930 A1 | 7/2013 | |
| WO | WO-2014036498 A2 * | 3/2014 | C08F 220/06 |
| WO | 2018237224 A1 | 12/2018 | |

* cited by examiner

UV CURE TOPCOATINGS FOR MEDICAL DEVICES

CROSS-REFERENCE

This application is a non-provisional application of and claims priority to and the benefit of U.S. Provisional Application No. 62/923,722, filed Oct. 21, 2019, which is incorporated herein by reference in its entirety.

TECHNICAL FIELD

The invention concerns ultraviolet light curable top coating for medical devices and implants.

BACKGROUND

The present invention relates to the field of non-thrombogenic and lubricious coatings that are applied to medical devices, especially devices intended to be implanted, temporarily or permanently, in the body and in blood-contact applications.

Among the many advances in medical practice in recent years is the development of medical devices that supplement the surgeon's skills. Examples of these are a variety of vascular catheters and guide wires that can be used to treat remote areas of the circulatory system otherwise available only by major surgery. Another is the stent, a device that reinforces arterial walls and prevents occlusion after angioplasty. Another is the intra-ocular lens that restores youthful eyesight to the elderly afflicted with cataracts. Heart valves, artificial pacemakers, and orthopedic implants are among a lengthening list of other such devices.

Nearly all of the above-described devices are constructed of plastics and metals that were never intended to invade and sometimes reside for prolonged periods in the human body. They present surfaces that bear little or no resemblance to those of human organs, which are generally hydrophilic, slippery and biocompatible.

Equally important for devices that must be inserted and moved through body tissues is their lubricity. Most metals and plastics have poor lubricity against body tissues, which results in mechanical abrasion and discomfort when the device is passed over the tissue.

The surfaces of devices designed and manufactured from such materials can be made biocompatible, as well as hydrophilic and slippery, by properly designed coatings. Thus, the way has been opened to construct medical devices from conventional plastics and metals having the particular physical properties required, and then to apply suitable coatings to impart the desired properties to their surfaces.

It has been shown that polymers that have low coefficients of friction when wet are water soluble polymers that are cross-linked or otherwise immobilized and swell, but do not dissolve, upon exposure to water. Polysaccharides have been shown to be useful in making hydrophilic, lubricious coatings on substrates. Such coatings are described in U.S. Pat. Nos. 4,801,475, 5,023,114, 5,037,677, and 6,673,453, the disclosures of which are hereby incorporated by reference. Lubricious coatings based upon polysaccharides exhibit exceptional biocompatibility and lubricity, but relatively poor resistance to ionizing radiation.

It is desirable for some applications to have a lubricious coating made of a synthetic polymer for the benefits of a longer shelf-life and stability to radiation-sterilization processes. Hydrophilic synthetic polymers, such as poly(acrylic acid) and its copolymers have often been proposed to make lubricious, hydrophilic coatings because of their ability to generate a hydrated layer on the surface.

Many attempts have been made to immobilize poly (acrylic acid) on surfaces so that they may be utilized as coatings on medical devices. The methods in U.S. Pat. Nos. 4,642,267 and 4,990,357 include physical blends of poly (acrylic acid) copolymer with a polyurethane dispersion. This method has the drawback that the interpolymer network physically attaching the hydrophilic polymer to the substrate surface often breaks down upon prolonged turbulent flow or soaking and the hydrophilic species may be washed away thereby rendering the article insufficiently lubricious.

Other methods invented to utilize poly(acrylic acid) as a hydrophilic coating on a surface include radiation grafting of a carboxylic acid monomer and its polymer as described in U.S. Pat. Nos. 2,999,056, 5,531,715, 5,789,018, and 6,221,061, and EP 0669837, plasma grafting of an acrylic acid monomer in EP 0220919, and also methods using a primer layer containing isocyanate, aziridine, amine and hydroxyl functional groups to anchor polyacrylic acid as stated in U.S. Pat. Nos. 5,091,205, 5,509,899, 5,702,754, 6,048,620, 6,558,798, 6,709,706, 6,087,416, 6,534,559, and EP 0379156, EP 0480809, EP 0728487, and EP 0963761. The disclosures of all the above-mentioned patents are hereby incorporated by reference.

The above-mentioned poly(acrylic acid) coatings exhibit relatively poor lubricity and/or durability because of insufficient hydrophilic polymer coating thickness and/or poor binding to the surface. It is difficult to achieve a high-density surface coverage by either grafting through photo-initiated polymerization or surface chemical attachment of polymers. Multiple-repeated coating processes may increase the thickness of photo-initiated polymerization coating, but will greatly decrease productivity and add to the cost of manufacturing.

Using a cross-linker can increase the thickness of a hydrophilic coating considerably. The prior art includes methods to cross-link polyacrylic acid coatings by photo radiation and by the reaction of polyfunctional reactive compounds, such as melamine and aziridines, as described in U.S. Pat. Nos. 5,531,715, 6,558,798, and EP 533821. However, the cross-linked hydrophilic coatings in the art often face a trade-off between lubricity and abrasion resistance, which are both indispensable properties for a hydrophilic coating. A highly cross-linked coating has poor lubricity because of its low capacity for hydration and reduced mobility of polymer segments in aqueous media. A coating with a low cross-linking density has a high swelling ratio, which generally leads to poor abrasion resistance and weak mechanical strength.

U.S. Patent Application Pub. No. 2011/0200828 teaches a bilaminar coating that includes a basecoat that firmly adheres to the substrate and a topcoat that is chemically grafted to the basecoat. The topcoat comprises a mixture of a water-soluble polymer containing carboxylic acid groups and a water-soluble chromium (III) compound. The coating forms a very durable, lubricious layer when wet. However, the carboxylate anion comprising the coating shows poor performance in thrombogenicity tests, such as the partial thromboplastin time (PTT) test. The disclosure of the above-cited reference is hereby incorporated by reference.

Contacting blood with a foreign object having a plastic or metal surface induces a complex set of clot-forming reactions that occur at the blood surface interface. Thromboembolism is a major complication associated with the clinical use of artificial devices, such as catheters, guidewires, mechanical heart valves, ventricular assist devices, implantable artificial hearts, vascular grafts, etc. In particular, thromboembolism is an important complication of angiographic procedures, particularly with catheter and guidewire manipulations proximal to the brachiocephalic vessels.

Surface modification is commonly used to make the materials more blood-compatible, while minimizing any loss of mechanical properties. Two approaches to modification have been commonly used. Suppression of nonspecific protein adsorption using coatings of polyethylene oxide (PEO) (a neutral, hydrophilic, and highly flexible polymer) or other hydrophilic polymers has been investigated for surface passivation. Uncontrolled, nonspecific protein adsorption, which usually occurs within seconds following the exposure of a foreign surface to blood, can initiate blood coagulation and the complement pathways.

A second approach has been to use coatings that actively assist the anticoagulant activity of surfaces. Certain plasma proteins such as antithrombin (AT) which can inhibit thrombin and factor Xa (FXa)) or heparin (a glycosaminoglycan which catalyzes the reactions of plasma AT) have been used for this purpose. Frech et al., in "A Simple Noninvasive Technique to Test Nonthrombogenic Surfaces," The American Journal of Roentgenology, vol. 113 (1971), p. 765-768, discloses coating of a guidewire with a benzalkonium-heparin complex. Ovitt et al., in "Guidewire Thrombogenicity and Its Reduction", Radiology, vol. 111 (1974), p. 43-46, reports Teflon coated guidewires treated with benzalkoniumheparin. U.S. Pat. No. 4,349,467 (William) shows the application of heparin to solid polymeric resin substrates by steeping the substrate in a solution of ammonium salt and contacting the substrate with a heparin salt solution.

There have also been many attempts to invent hydrophilic polymers with applications ranging from electrophoresis, hair treatment and paper treatment. As revealed by Albarghouthi et al, in "Poly-N-hydroxyethylacrylamide(polyDuramide): A novel, hydrophilic, self-coating polymer matrix for DNA sequencing by capillary electrophoresis", Electrophoresis, vol. 23 (2002), p. 1429-1440, non-ionic monomers, such as N-hydroxyethyl acrylamide, have great hydrophilicity.

The following references, namely WO10041527A, WO10041530A, WO11125713A, JP2011046619A, JP2011046652A, JP2010126482A, and JP2010090049A, teach copolymers comprised of a 5-30 mol % of a carboxylic acid monomer and 70-95 mol % of an alcohol containing acrylic monomer for use in hair treatment formulations. These patent applications do not disclose the utility of the copolymers as lubricious, biocompatible coatings nor do they disclose their resistance to ionizing radiation. JP2006176934A teaches copolymers from methacrylamide, hydroxyethyl acrylamide, and an ionic vinyl monomer for use as an additive to increase the strength of the paper. The latter reference does not disclose the utility of the copolymers as lubricious, biocompatible coatings nor does it disclose their resistance to ionizing radiation.

SUMMARY

The invention concerns coating compositions for medical devices or medical implants comprising a polymer which is soluble in water or water-alcohol solutions, the polymer made from monomers comprising: (a) at least one monomer that is a photo radical generator, and (b) at least one monomer comprising one or both of (i) ethylenic monomers comprising at least one acidic group and (ii) one or more of acrylates or acrylamides; wherein the molar ratio of one or both of (i) ethylenic monomers comprising at least one acidic group and (ii) one or more of acrylates or acrylamides to photo radical generator group is 20:1 to 500:1.

The invention also concerns coated substrates comprising a substrate and a lubricious coating made using a coating composition described herein.

Additional embodiments concern coating a composition described herein in an aqueous solution.

Yet other embodiments include medical devices or implants where a lubricious coating contains a pharmaceutical or antimicrobial agent blended with the coating composition.

DETAILED DESCRIPTION OF ILLUSTRATIVE EMBODIMENTS

The requirements for any coating intended for use on medical devices will be set forth and explained first. The specification will then show how the present invention fulfills these requirements.

The coatings of the instant invention are suitable for use in medical devices. The coatings of the present invention have the following properties:

(1) the coating must be able, on drying, to form a continuous, adherent film of good integrity on the surface of the material to be coated. This means that the minimum film-forming temperature of the coating solution must be lower than the expected drying temperature to be used during device fabrication;

(2) the formed polymer film must be flexible and adherent enough to conform without rupture to the bending and twisting of the coated device under the expected conditions of use;

(3) when the coated device is immersed for long periods in aqueous media such as human blood, the film must not weaken or lose its integrity;

(4) the coating must present a non-cytotoxic and blood compatible surface. When contacted with human blood the coating must not initiate blood coagulation and the complement pathways;

(5) the coating must be firmly and securely bound to the substrate so that no particles or fragments or leachable components can contaminate an aqueous medium such as human blood; and (6) the coating must withstand some acceptable form of sterilization without loss of integrity, durability, biocompatibility or lubricity.

In some embodiments, the invention concerns coating compositions for medical devices or medical implants comprising a polymer which is soluble in water or water-alcohol solutions, the polymer made from monomers comprising:

(a) at least one monomer that is a photo radical generator, and (b) at least one monomer comprising one or both of (i) ethylenic monomers comprising at least one acidic group and (ii) one or more of acrylates or acrylamides; wherein the molar ratio of one or both of (i) ethylenic monomers comprising at least one acidic group and (ii) one or more of acrylates or acrylamides to photo radical generator group is 20:1 to 500:1.

The polymer may be packaged in a water or water-alcohol mixture. The alcohol is typically a $C_1$-$C_6$ alcohol. Preferred alcohols include methanol, ethanol and iso-propanol. The ratio of water to alcohol can be 100:0 to 50:50.

Some preferred photo radical generators are benzophenone compounds. In some embodiments, the photo radical generator is selected from one or more of comprises one or more of 4-methacryloxy-2-hydroxybenzophenone, 4-acryloxybenzophenone, 4-methacryloxybenzophenone, acrylamidobenzophenone, methacrylamidobenzophenone, 2-hydroxy-4-acryloxyethoxybenzophenone, 2,4-dihydroxy-4'-vinyl benzophenone, and 2-hydroxy-4-methacryloxyethoxybenzophenone. One preferred photo radical generator group comprises 4-methacryloxy-2-hydroxybenzophenone.

A variety of ethylenic monomers may be used. In some embodiments the monomers comprise at least one acidic group comprises acrylic acid, methacrylic acid, 2-ethylacrylic acid, 2-propylacrylic acid, acryloxypropionic acid, isocrotonic acid, maleic anhydride, maleic acid and half esters, half amides and half thioesters of maleic acid, fumaric acid and itaconic acid, and mixtures thereof. In some embodiments, the ethylenic monomers comprise N-(2-hydroxyethyl)acrylamide and acrylic acid. In certain embodiments, the molar ratio of N-(2-hydroxyethyl)acrylamide to acrylic acid is 2:1 to 5:1.

Preferred acrylates and acrylamides include acrylamide, N-(2-hydroxyethyl)acrylamide, 2-hydroxyethyl methacrylate, 2-hydroxypropyl acrylate, 2-hydroxypropyl methacrylate, and N-(2-hydroxyethyl) methacrylamide, N-acryloylamido-ethoxyethanol, N-(hydroxymethyl) acrylamide, N-[tris(hydroxymethyOmethyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, or any mixture of the foregoing.

In some embodiments, the molar ratio of one or both of (i) ethylenic monomers comprising at least one acidic group and (ii) one or more of acrylates or acrylamides to photo radical generator comprising at least one photopolymerizable group is 40:1 to 200:1.

In certain embodiments, the polymer has a weight-average molecular weight (Mw) of between 20,000 and 800,000 or 20,000 to 400,000 or 50,000 and 400,000.

Some coating compositions additionally comprise a second polymer which is soluble in water or water-alcohol solutions. In some embodiments, the second polymer comprises one or both of (i) ethylenic monomers comprising at least one acidic group and (ii) one or more of acrylates or acrylamides. In the second polymer, the ethylenic monomers of the second polymer comprise at least one acidic group, the ethylenic monomers of the second polymer comprising the at least one acidic group comprise one or more of acrylic acid, methacrylic acid, 2-ethylacrylic acid, 2-propylacrylic acid, acryloxypropionic acid, isocrotonic acid, maleic anhydride, maleic acid and half esters, half amides and half thioesters of maleic acid, fumaric acid, itaconic acid, and any combination thereof. Additionally, in the second polymer the acrylates or acrylamides comprise acrylamide, N-(2-hydroxyethyl)acrylamide, 2-hydroxyethyl methacrylate, 2-hydroxypropyl acrylate, 2-hydroxypropyl methacrylate, and N-(2-hydroxyethyl) methacrylamide, N-acryloylamido-ethoxyethanol, N-(hydroxymethyl) acrylamide, N-[tris(hydroxymethyl)methyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, and any mixture of the foregoing.

In some embodiments, the second polymer has a weight-average molecular weight (Mw) of between 50,000 and 800,000.

The invention also concerns coated substrates comprising a substrate and a lubricious coating made using a coating composition described herein. Preferred embodiments, additionally comprise a basecoat that contacts both the substrate and the lubricious coating composition. Preferred basecoats are hydrophobic.

The coatings may be used on any medical device or implant suitable for the coating's application. In some embodiments, the substrate is plastic or metallic.

Preferred coated substrates have a lubricity of less than 25 gf friction and a durability of less than 50 gf friction as measured by a pinch test.

The invention also concerns medical devices and medical implants comprising a coated substrate described herein. In some embodiments, the medical device or medical implant is sterilized by at least one of gamma-ray, E-beam, and ethylene oxide.

In additional embodiments, the coatings described herein contain a pharmaceutical or antimicrobial agent blended with the coating composition.

4-Methacryloxy-2-hydroxy benzophenone (MHB) can be copolymerized with polar acrylates such as Acrylic Acid and N-(2-Hydroxyethyl)acrylamide to produce a hydrophilic, photoactive polymer. Upon ultraviolet (UV) cure this polymer functions as a lubricious topcoat. It can also be used as an additive to other hydrophilic (non-photoactive) polymers to form a lubricious coating after UV Cure.

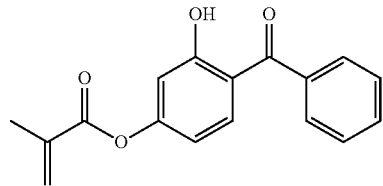

4-methacryloxy-2-hydroxy benzophenone (MHB)

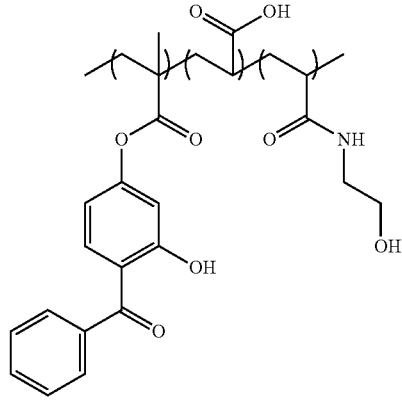

Random copolymer of MHB, Acrylic Acid, and N-(2-Hydroxyethyl)acrylamide

The invention relates to at least the following aspects.

Aspect 1. A coating composition for medical devices or medical implants comprising a polymer which is soluble in water or water-alcohol solutions, the polymer made from monomers comprising: (a) at least one monomer that is a photo radical generator comprising one or more of 4-methacryloxy-2-hydroxybenzophenone, 4-acryloxybenzophenone, 4-methacryloxybenzophenone, acrylamidobenzophenone, methacrylamidobenzophenone, 2-hydroxy-4-acryloxyethoxybenzophenone, 2,4-dihydroxy-4'-vinyl benzophenone, and 2-hydroxy-4-methacryloxyethoxybenzophenone, and (b) at least one monomer comprising one or both of (i) ethylenic monomers comprising at least one acidic group and (ii) one or more of acrylates or acrylamides; wherein the ethylenic monomers comprise at least one acidic group comprises acrylic acid, methacrylic acid, 2-ethylacrylic acid, 2-propylacrylic acid, acryloxypropionic acid, isocrotonic acid, maleic anhydride, maleic acid and half esters, half amides and half thioesters of maleic acid, fumaric acid and itaconic acid, and mixtures thereof; wherein the acrylates or acrylamides comprise acrylamide, N-(2-hydroxyethyl)acrylamide, 2-hydroxyethyl methacrylate, 2-hydroxypropyl acrylate, 2-hydroxypropyl methacrylate, and N-(2-hydroxyethyl) methacrylamide, N-acryloylamido-ethoxyethanol, N-(hydroxymethyl) acrylamide, N-[tris(hydroxymethylOmethyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, or any mixture of the foregoing; wherein the molar ratio of one or both of (i) ethylenic monomers comprising at least one acidic group and (ii) one or more of acrylates or acrylamides to photo radical generator group is 20:1 to 500:1.

Aspect 2. The coating composition of claim 1, wherein the photo radical generator group comprises 4-methacryloxy-2-hydroxybenzophenone.

Aspect 3. The coating composition of claim 1, wherein the ethylenic monomers comprise N-(2-hydroxyethyl)acrylamide and acrylic acid.

Aspect 4. The coating composition of claim 3, wherein the molar ratio of N-(2-hydroxyethyl)acrylamide to acrylic acid is 2:1 to 5:1.

Aspect 5. The coating composition of claim 1, wherein the molar ratio of one or both of (i) ethylenic monomers comprising at least one acidic group and (ii) one or more of acrylates or acrylamides to photo radical generator comprising at least one photopolymerizable group is 40:1 to 200:1.

Aspect 6. The coating composition of claim 1, wherein the polymer has a weight-average molecular weight (Mw) of between 20,000 and 800,000.

Aspect 7. The coating composition of claim 1, additionally comprising a second polymer which is soluble in water or water-alcohol solutions.

Aspect 8. The coating composition of claim 7, comprising one or both of (i) ethylenic monomers comprising at least one acidic group and (ii) one or more of acrylates or acrylamides.

Aspect 9. The coating composition of claim 8, wherein the ethylenic monomers of the second polymer comprise at least one acidic group, the ethylenic monomers of the second polymer comprising the at least one acidic group comprise one or more of acrylic acid, methacrylic acid, 2-ethylacrylic acid, 2-propylacrylic acid, acryloxypropionic acid, isocrotonic acid, maleic anhydride, maleic acid and half esters, half amides and half thioesters of maleic acid, fumaric acid, itaconic acid, and any combination thereof.

Aspect 10. The coating composition of claim 8, wherein the acrylates or acrylamides of the second polymer comprise acrylamide, N-(2-hydroxyethyl)acrylamide, 2-hydroxyethyl methacrylate, 2-hydroxypropyl acrylate, 2-hydroxypropyl methacrylate, and N-(2-hydroxyethyl) methacrylamide, N-acryloylamido-ethoxyethanol, N-(hydroxymethyl) acrylamide, N-[tris(hydroxymethyl)methyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, and any mixture of the foregoing.

Aspect 11. The coating composition of claim 8, wherein the second polymer has a weight-average molecular weight (Mw) of between 50,000 and 800,000.

Aspect 12. The coating composition of claim 1, additionally comprising water or a water/alcohol mixture.

Aspect 13. A coated substrate comprising: a substrate and a lubricious coating made using a coating composition of any one of claims 1-12.

Aspect 14. The coated substrate of claim 13, additionally comprising a base coat that contacts both the substrate and the lubricious coating composition.

Aspect 15. The coated substrate of claim 14, wherein the base coat is hydrophobic.

Aspect 16. The coated substrate of claim 13, wherein the substrate is plastic.

Aspect 17. The coated substrate of claim 13, wherein the substrate is metallic.

Aspect 18. The coated substrate of any one of claims 13-17, wherein the coated substrate has a lubricity of less than 25 gf friction and a durability of less than 50 gf friction as measured by a pinch test.

Aspect 19. A medical device or medical implant comprising a coated substrate of any one of claims 13-18.

Aspect 20. The medical device or medical implant of claim 19 where the medical device or medical implant is sterilized by at least one of gamma-ray, E-beam, and ethylene oxide.

Aspect 21. The medical device or medical implant of claim 19 or 20, where the lubricious coating contains a pharmaceutical or antimicrobial agent blended with the coating composition.

EXAMPLES

The invention is illustrated by the following non-limiting examples.

Materials. 4-methacryloxy-2-hydroxy benzophenone (MHB) was purchased from Polysciences and Bimax. Purity of MHB was confirmed with nuclear magnetic resonance NMR. All other chemicals were purchased from approved suppliers and IR spectra were taken on Perkin Elmer Frontier FT-IR Spectrometer with a Universal ATR Sampling Accessory. NMRs were done at USciences with a Bruker 400 MHz NMR.

Poly(HEAA-co-AA) in Table 1. The polymer was made by reacting 29.79 g of N-(2-hydroxyethyl)acrylamide (HEAA), 6.21 g of acrylic acid (AA) in 263 milliliters (mL) of water. The initiator for the polymerization was ammonium persulfate and sodium hydroxymethansulfinate hydrate. 0.015 mL of a 1% solution of iron(II) sulfate $FeSO_4$ was added to catalyze the reaction. The polymerization was done under $N_2$ at 40° C. The polymer was purified by dialysis or precipitation with acetone (similar to Example 1 of US2013/0323291 A1).

Poly(HEAA-co-AA-co-MHB) 1-4 in Table 1. The photoactive polymer was made by reacting 15.29 g of HEAA, 3.19 g of AA and 1.00 g, 0.50 g, or 0.25 g of MHB in 40 mL of IPA and 30 mL of water. 0.59 mL of a 50 milligrams per milliliter (mg/mL) solution of Azobisisobutyronitrile (AiBN) in THF was added to the monomer solution. The solution was sparged for 30 minutes to remove the oxygen, then heated to 60° C. for 24 hours. After the reaction was complete the polymer was precipitate with 150 mL of ethyl acetate. The solvent was decanted off and the polymer then dried in an oven at 60° C. with any remaining solvent being removed under vacuum. The polymer was dissolved in a 50:50 mixture of IPA and water.

Poly(HEAA-co-AA-co-MHB) 5-7 in Table 1. The photoactive polymer was made by reacting 15.29 grams (g) of HEAA, 3.19 g of AA and 1.00 g, 0.50 g or 0.25 g of MHB in 40 mL of ethanol and 30 mL of water. 0.245 mL of a 20 mg/mL solution of (AiBN) in THF was added to the monomer solution. The solution was sparged for 30 minutes to remove the oxygen then heated to 60° C. for 24 hours. After the reaction was complete the polymer was precipitate with 150 mL of ethyl acetate. The solvent was decanted off and the polymer then dried in an oven at 60° C. with any remaining solvent removed under vacuum. The polymers were dissolved in a 50:50 mixture of ethanol and water.

The molecular weights were determined through SEC using a Waters 1515 isocratic high performance liquid chromatography HPLC pump, Waters 2489 UV/Visible detector set to 276 nanometers (nm) and 290 nm, Waters 2414 Refractive Index Detector, and 3 columns (2 Waters Ultrahydrogel 2000 and 1 Waters Ultrahydrogel 250). The molecular weights were calculated by comparing to poly (acrylic acid) standards using Empower 3 software.

The coating was applied to a Pebax™ 55D plastic tubing using the dip-coating method. The Pebax™ tubing had an outer diameter of 0.079 inches and a wall thickness of 0.005 inches. The tubing was placed over stainless steel rod for stability. The tubing was first dipped into the basecoat and extracted at 0.2 inches per second and was rotated in UV chamber for 5 minutes set to the desired intensity. Then the tubing was dipped into the topcoat and extracted at 0.2 inches per second and was rotated in UV chamber for 5 minutes set to the desired intensity.

UV cure was performed in an Uvitron IntelliRay model UV0832 UV Cure unit equipped with a UVA 600 Watt metal halide lamp. Irradiance was measured with an EIT Uvicure Plus II radiometer purchased from INPRO Technologies. This one channel UVA radiometer measures the radiation between 320 and 390 nm.

The friction of the coating was pinch tested on a Tinius Olsen 5ST Electromechanical Testing Machine with a 10N load cell and the data was collected with Horizon software. The Tinius Olsen is equipped with a heated water bath and pinch pads that pressed together at a constant force. The water bath is filled with PBS solution and heated to 37° C. The pinch pads are submerged in the water and pressed together with 450 g of force. The friction is measured as the grams of force required to push and pull the sample through the pads. The lubricity and durability are determined by averaging the grams of force when the samples are pulled through the pads. Lubricity is the average from cycle 2-4 and durability is the average from cycle 28-30.

Basecoat solutions were made using two different photoactive basecoat polymers. The Basecoat polymer can be diluted with a variety of different solvents including Isopropanol (IPA) and Ethanol. Basecoat A: 10 wt % solution of a copolymer of 2-ethylhexyl methacrylate (EHMA), N-vinylpyrrolidone (NVP), (hydroxyethyl)methacrylate (HEMA), and MHB in propylene glycol methyl ether acetatePMA with a polyaziridine crosslinker. Basecoat B: 10 wt % solution of a copolymer of butyl acrylate (BA), methyl methacrylate (MMA), NVP, HEMA, and MHB in PMA with a polyaziridine crosslinker.

TABLE 1

Lists the composition and $M_w$ and $M_n$ for the polymers made and tested.

| Poly(HEAA-co-AA-co-MHB) | Mole % MHB | $M_w$ | $M_n$ | $M_w/M_n$ |
|---|---|---|---|---|
| 1 | 2 | 72417 | 19150 | 3.78 |
| 2 | 1 | 58864 | 12757 | 4.61 |
| 3 | 1 | 191290 | 55687 | 3.44 |
| 4 | 0.5 | 216586 | 74642 | 2.94 |
| 5 | 2 | 218178 | 79888 | 2.73 |
| 6 | 1 | 254733 | 69063 | 3.69 |
| 7 | 0.5 | 231294 | 75766 | 3.05 |
| Poly(HEAA-co-AA) | 0 | 649456 | 301998 | 2.15 |

TABLE 2

Shows the results of the friction test of the different topcoats and UV light intensity using A as the Basecoat. The photo-active topcoat contained a Poly(HEAA-co-AA-co-MHB) described in table 1, Poly(HEAA-co-AA), and surfactants in water.

| | Basecoat | Poly(HEAA-co-AA-co-MHB) (Wt %) | Poly(HEAA-co-AA) (Wt %) | Intensity (mW/cm$^2$) | Lubricity (gf) | Durability (gf) | Pads |
|---|---|---|---|---|---|---|---|
| 1 | A | 1% (19 kMn/2% MHB) | 2% | 130 | 14 ± 0.8 | 14 ± 1.0 | Silicone |
| 2 | A | 1% (19 kMn/2% MHB) | 2% | 90 | 10 ± 0.9 | 13 ± 0.2 | Silicone |
| 3 | A | 1% (19 kMn/2% MHB) | 2% | 90 | 12 ± 0.2 | 17 ± 6.1 | Delrin |
| 4 | A | 0.5% (19 kMn/2% MHB) | 2% | 90 | 12 ± 0.6 | 14 ± 2.6 | Delrin |
| 5 | A | 1% (13 kMn/1% MHB) | 2% | 90 | 12 ± 4.0 | 25 ± 13 | Delrin |
| 6 | A | 1% (56 kMn/1% MHB) | 2% | 90 | 19 ± 3.7 | 45 ± 20 | Delrin |
| 7 | A | 0.5% (56 kMn/1% MHB) | 2% | 90 | 15 ± 1.6 | 41 ± 3.1 | Delrin |

TABLE 2-continued

Shows the results of the friction test of the different topcoats and UV light intensity using A as the Basecoat. The photo-active topcoat contained a Poly(HEAA-co-AA-co-MHB) described in table 1, Poly(HEAA-co-AA), and surfactants in water.

| | Basecoat | Poly(HEAA-co-AA-co-MHB) (Wt %) | Poly(HEAA-co-AA) (Wt %) | Intensity (mW/cm$^2$) | Lubricity (gf) | Durability (gf) | Pads |
|---|---|---|---|---|---|---|---|
| 8 | A | 1% (75 kMn/0.5% MHB) | 2% | 90 | 18 ± 8.3 | 116 ± 105 | Delrin |
| 9 | A | 1% (69 kMn/1% MHB) | 2% | 90 | 14 ± 1.2 | 16 ± 6.4 | Delrin |
| 10 | A | 0.5% (69 kMn/1% MHB) | 2% | 90 | 16 ± 2.8 | 44 ± 32 | Delrin |
| 11 | A | 1% (69 kMn/1% MHB) | 2% | 130 | 12 ± 0.8 | 26 ± 7.6 | Delrin |
| 12 | A | 0.5% (69 kMn/1% MHB) | 2% | 130 | 14 ± 2.3 | 31 ± 11 | Delrin |
| 13 | A | 1% (80 kMn/2% MHB) | 2% | 90 | 11 ± 1.6 | 85 ± 9.2 | Delrin |
| 14 | A | 0.5% (80 kMn/2% MHB) | 2% | 90 | 13 ± 4.0 | 111 ± 25 | Delrin |
| 15 | A | 1% (80 kMn/2% MHB) | 2% | 130 | 16 ± 5.4 | 105 ± 34 | Delrin |
| 16 | A | 0.5% (80 kMn/2% MHB) | 2% | 130 | 13 ± 5.8 | 75 ± 33 | Delrin |
| 17 | A | 1% (76 kMn/0.5% MHB) | 2% | 90 | 13 ± 4.0 | 144 ± 69 | Delrin |
| 18 | A | 1% (76 kMn/0.5% MHB) | 2% | 130 | 12 ± 2.2 | 16 ± 10 | Delrin |

TABLE 3

Show the results of the friction test of the different topcoats. Coated two times with topcoat and no basecoat. The photo-active topcoat contained a Poly(HEAA-co-AA-co-MHB) described in table 1, Poly(HEAA-co-AA), and surfactants in water.

| | Poly(HEAA-co-AA-co-MHB) (Wt %) | Poly(HEAA-co-AA) Wt % | Intensity (mW/cm$^2$) | Lubricity (gf) | Durability (gf) | Pads |
|---|---|---|---|---|---|---|
| 1 | 1% (19 kMn/2% MHB) | 2% | 130 | 12 ± 1.4 | 15 ± 1.8 | Silicone |
| 2 | 1% (19 kMn/2% MHB) | 2% | 90 | 9 ± 2.3 | 100 ± 74 | Silicone |
| 3 | 1% (19 kMn/2% MHB) | 2% | 130 | 52 ± 6.8 | 158 ± 3.7 | Delrin |
| 4 | 1% (19 kMn/2% MHB) | 2% | 90 | 51 ± 6.4 | 132 ± 14 | Delrin |
| 5 | 1% (69 kMn/1% MHB) | 2% | 130 | 6 ± 4.5 | 76 ± 57 | Silicone |
| 6 | 1% (69 kMn/1% MHB) | 2% | 90 | 5 ± 1.1 | 29 ± 36 | Silicone |
| 7 | 1% (69 kMn/1% MHB) | 2% | 130 | 29 ± 8.3 | 104 ± 20 | Delrin |
| 8 | 1% (69 kMn/1% MHB) | 2% | 90 | 51 ± 6.6 | 108 ± 3.2 | Delrin |

TABLE 4

Show the results of the friction test of the different topcoats using Basecoat B. The photo-active topcoat contained a Poly(HEAA-co-AA-co-MHB) described in table 1, Poly(HEAA-co-AA), and in water.

| | Basecoat | Poly(HEAA-co-AA-co-MHB) (Wt %) | Poly(HEAA-co-AA) (Wt %) | IPA (Wt %) | Intensity (mW/cm$^2$) | Lubricity (gf) | Durability (gf) | Pads |
|---|---|---|---|---|---|---|---|---|
| 1 | B | 1% (19 kMn/2% MHB) | 2% | none | 90 | 36 ± 9.8 | 50 ± 26 | Delrin |
| 2 | B | 1% (19 kMn/2% MHB) | 2% | 10 | 90 | 9.6 ± 1.4 | 10 ± 0.2 | Delrin |

TABLE 4-continued

Show the results of the friction test of the different topcoats using Basecoat B. The photo-active topcoat contained a Poly(HEAA-co-AA-co-MHB) described in table 1, Poly(HEAA-co-AA), and in water.

| | Basecoat | Poly(HEAA-co-AA-co-MHB) (Wt %) | Poly(HEAA-co-AA) (Wt %) | IPA (Wt %) | Intensity (mW/cm$^2$) | Lubricity (gf) | Durability (gf) | Pads |
|---|---|---|---|---|---|---|---|---|
| 3 | B | 0.5% (19kMn/2% MHB) | 2% | none | 90 | 38 ± 2.3 | 83 ± 67 | Delrin |
| 4 | B | 0.5% (19 kMn/2% MHB) | 2% | 10 | 90 | 14 ± 1.3 | 15 ± 1.3 | Delrin |
| 5 | B | 1% (80 kMn/2% MHB) | 2% | 10 | 90 | 16 ± 5.9 | 20 ± 12 | Delrin |

Throughout this specification, words are to be afforded their normal meaning, as would be understood by those skilled in the relevant art, unless otherwise indicated. However, so as to avoid misunderstanding, the meanings of certain terms will be specifically defined or clarified.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value.

Where present, all ranges are inclusive and combinable. That is, references to values stated in ranges include every value within that range including the endpoint values.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A and B," "A and C," "B and C," or "A, B, and C."

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other possible embodiment(s) and such a combination is considered to be another embodiment. Conversely, various features of the invention that are, for brevity, described in the context of a single embodiment, may also be provided separately or in any sub-combination. Further, while an embodiment may be described as part of a series of steps or part of a more general structure, each said step or part may also be considered an independent embodiment in itself.

As used herein, the terms "article" and "substrate" are not limited to any shape or size, as it may be a layer of material, multiple layers or a block having at least one surface of which is modified by a coating composition described herein.

As used herein the term "hydrophobic" is characterized by the lack of solubility of the non-crosslinked polymer in water.

The term "hydrophilic" refers to a substrate surface made of a polymer where the uncured or non-crosslinked polymer is soluble in water or in a water alcohol solution that is more than 50% water.

Unless otherwise specified, all molecular weights are weight-average molecular weights (Mw).

What is claimed:

1. A coating composition for medical devices or medical implants comprising a random polymer which is soluble in water or water-alcohol solutions, the polymer made from monomers consisting essentially of:
   (a) at least one monomer that is a photo radical generator comprising one or more of 4-methacryloxy-2-hydroxybenzophenone, 4-acryloxybenzophenone, 4-methacryloxybenzophenone, acrylamidobenzophenone, methacrylamidobenzophenone, 2-hydroxy-4-acryloxyethoxybenzophenone, and 2-hydroxy-4-methacryloxyethoxybenzophenone, and
   (b) (i) at least one monomer comprising ethylenic monomers comprising at least one acidic group; and (ii) at least one monomer comprising one or more of acrylates or acrylamides, provided one monomer is N-(2-hydroxyethyl)acrylamide;
   wherein the ethylenic monomers comprise acrylic acid;
   wherein the acrylates or acrylamides comprise acrylamide, N-(2-hydroxyethyl)acrylamide, 2-hydroxyethyl methacrylate, 2-hydroxypropyl acrylate, 2-hydroxypropyl methacrylate, and N-(2-hydroxyethyl) methacrylamide, N-acryloylamido-ethoxyethanol, N-(hydroxymethyl) acrylamide, N-[tris(hydroxymethyl) methyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bisacrylamide, N,N-1,2-dihydroxyethylene-bis-methyacrylamide, N-hydroxymethyl methacrylamide, N-tri (hydroxymethyl)-methyl-methacrylamide, or any mixture of the foregoing;
   wherein the molar ratio of both of (i) ethylenic monomers comprising at least one acidic group and (ii) one or more of acrylates or acrylamides to (a) monomers comprising a photo radical generator is 20:1 to 500:1.

2. The coating composition of claim 1, wherein the polymer is made from monomers consisting of:
   (a) at least one monomer that is a photo radical generator comprising one or more of 4-methacryloxy-2-hydroxybenzophenone, 4-acryloxybenzophenone, 4-methacryloxybenzophenone, acrylamidobenzophenone, methacrylamidobenzophenone, 2-hydroxy-4-acryloxyethoxybenzophenone, and 2-hydroxy-4-methacryloxyethoxybenzophenone, and
   (b) (i) at least one monomer comprising ethylenic monomers comprising at least one acidic group; and (ii) at least one monomer comprising one or more of acrylates or acrylamides, provided one monomer is N-(2-hydroxyethyl)acrylamide;
   wherein the ethylenic monomers comprise and acrylic acid;
   wherein the acrylates or acrylamides comprise acrylamide, N-(2-hydroxyethyl)acrylamide, 2-hydroxyethyl methacrylate, 2-hydroxypropyl acrylate, 2-hydroxypropyl methacrylate, and N-(2-hydroxyethyl) methacrylamide, N-acryloylamido-ethoxyethanol, N-(hydroxymethyl) acrylamide, N-[tris(hydroxymethyl)methyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, or any mixture of the foregoing;
   wherein the molar ratio of both of (i) ethylenic monomers comprising at least one acidic group and (ii) one or more of acrylates or acrylamides to (a) monomers comprising a photo radical generator is 20:1 to 500:1.

3. The coating composition of claim 1, wherein the photo radical generator comprises 4-methacryloxy-2-hydroxybenzophenone.

4. The coating composition of claim 1, wherein the molar ratio of N-(2-hydroxyethyl)acrylamide to acrylic acid is 2:1 to 5:1.

5. The coating composition of claim 1, wherein the molar ratio of both of (i) ethylenic monomers comprising at least one acidic group and (ii) one or more of acrylates or acrylamides to photo radical generator comprising at least one photopolymerizable group is 40:1 to 200:1.

6. A coating composition for medical devices or medical implants comprising a random polymer which is soluble in water or water-alcohol solutions, the polymer made from monomers consisting essentially of:
   (a) at least one monomer that is a photo radical generator comprising one or more of 4-methacryloxy-2-hydroxybenzophenone, 4-acryloxybenzophenone, 4-methacryloxybenzophenone, acrylamidobenzophenone, methacrylamidobenzophenone, 2-hydroxy-4-acryloxyethoxybenzophenone, and 2-hydroxy-4-methacryloxyethoxybenzophenone, and
   (b) (i) at least one monomer comprising ethylenic monomers comprising at least one acidic group; and (ii) at least one monomer comprising one or more of acrylates or acrylamides;
   wherein the ethylenic monomers comprising at least one acidic group comprises acrylic acid, methacrylic acid, 2-ethylacrylic acid, 2-propylacrylic acid, acryloxypropionic acid, isocrotonic acid, maleic anhydride, maleic acid and half esters, half amides and half thioesters of maleic acid, fumaric acid and itaconic acid, and mixtures thereof;
   wherein the acrylates or acrylamides comprise acrylamide, N-(2-hydroxyethyl)acrylamide, 2-hydroxyethyl methacrylate, 2-hydroxypropyl acrylate, 2-hydroxypropyl methacrylate, and N-(2-hydroxyethyl) methacrylamide, N-acryloylamido ethoxyethanol, N-(hydroxymethyl) acrylamide, N-[tris(hydroxymethyl)methyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, or any mixture of the foregoing;
   wherein the molar ratio of both of (i) ethylenic monomers comprising at least one acidic group and (ii) one or more of acrylates or acrylamides to (a) monomers comprising a photo radical generator is 20:1 to 500:1;
   wherein the polymer has a weight-average molecular weight (Mw) of between 20,000 and 800,000.

7. The coating composition of claim 1, additionally comprising a second polymer which is soluble in water or water-alcohol solutions.

8. The coating composition of claim 7, wherein the ethylenic monomers of the second polymer comprise at least one acidic group, the ethylenic monomers of the second polymer comprising the at least one acidic group comprise one or more of acrylic acid, methacrylic acid, 2-ethylacrylic acid, 2-propylacrylic acid, acryloxypropionic acid, isocrotonic acid, maleic anhydride, maleic acid and half esters, half amides and half thioesters of maleic acid, fumaric acid, itaconic acid, and any combination thereof.

9. The coating composition of claim 7, wherein the acrylates or acrylamides of the second polymer comprise acrylamide, N-(2-hydroxyethyl)acrylamide, 2-hydroxyethyl methacrylate, 2-hydroxypropyl acrylate, 2-hydroxypropyl methacrylate, N-(2-hydroxyethyl) methacrylamide, N-acryloylamido-ethoxyethanol, N-(hydroxymethyl) acrylamide, N-[tris(hydroxymethyl)methyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, and any mixture of the foregoing.

10. A coating composition for medical devices or medical implants comprising a random polymer which is soluble in water or water-alcohol solutions, the polymer made from monomers consisting essentially of:
   (a) at least one monomer that is a photo radical generator comprising one or more of 4-methacryloxy-2-hydroxybenzophenone, 4-acryloxybenzophenone, 4-methacryloxybenzophenone, acrylamidobenzophenone, methacrylamidobenzophenone, 2-hydroxy-4-acryloxyethoxybenzophenone, and 2-hydroxy-4-methacryloxyethoxybenzophenone, and
   (b) (i) at least one monomer comprising ethylenic monomers comprising at least one acidic group; and (ii) at least one monomer comprising one or more of acrylates or acrylamides;

wherein the ethylenic monomers comprising at least one acidic group comprises acrylic acid, methacrylic acid, 2-ethylacrylic acid, 2-propylacrylic acid, acryloxypropionic acid, isocrotonic acid, maleic anhydride, maleic acid and half esters, half amides and half thioesters of maleic acid, fumaric acid and itaconic acid, and mixtures thereof;

wherein the acrylates or acrylamides comprise acrylamide, N-(2-hydroxyethyl)acrylamide, 2-hydroxyethyl methacrylate, 2-hydroxypropyl acrylate, 2-hydroxypropyl methacrylate, and N-(2-hydroxyethyl) methacrylamide, N-acryloylamido-ethoxyethanol, N-(hydroxymethyl) acrylamide, N-[tris(hydroxymethyl)methyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, or any mixture of the foregoing;

wherein the molar ratio of both of (i) ethylenic monomers comprising at least one acidic group and (ii) one or more of acrylates or acrylamides to (a) monomers comprising a photo radical generator is 20:1 to 500:1;

additionally comprising a second polymer which is soluble in water or water-alcohol solutions;

wherein the second polymer has a weight-average molecular weight (Mw) of between 50,000 and 800,000.

11. The coating composition of claim 6, wherein the photo radical generator comprises 4-methacryloxy-2-hydroxybenzophenone.

12. The coating composition of claim 6, wherein the molar ratio of both of (i) ethylenic monomers comprising at least one acidic group and (ii) one or more of acrylates or acrylamides to photo radical generator comprising at least one photopolymerizable group is 40:1 to 200:1.

13. The coating composition of claim 6, additionally comprising a second polymer which is soluble in water or water-alcohol solutions.

14. The coating composition of claim 13, wherein the ethylenic monomers of the second polymer comprise at least one acidic group, the ethylenic monomers of the second polymer comprising the at least one acidic group comprise one or more of acrylic acid, methacrylic acid, 2-ethylacrylic acid, 2-propylacrylic acid, acryloxypropionic acid, isocrotonic acid, maleic anhydride, maleic acid and half esters, half amides and half thioesters of maleic acid, fumaric acid, itaconic acid, and any combination thereof.

15. The coating composition of claim 13, wherein the acrylates or acrylamides of the second polymer comprise acrylamide, N-(2-hydroxyethyl)acrylamide, 2-hydroxyethyl methacrylate, 2-hydroxypropyl acrylate, 2-hydroxypropyl methacrylate, N-(2-hydroxyethyl) methacrylamide, N-acryloylamido-ethoxyethanol, N-(hydroxymethyl) acrylamide, N-[tris(hydroxymethyl)methyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, and any mixture of the foregoing.

16. The coating composition of claim 10, wherein the photo radical generator comprises 4-methacryloxy-2-hydroxybenzophenone.

17. The coating composition of claim 10, wherein the molar ratio of both of (i) ethylenic monomers comprising at least one acidic group and (ii) one or more of acrylates or acrylamides to photo radical generator comprising at least one photopolymerizable group is 40:1 to 200:1.

18. The coating composition of claim 10, wherein the ethylenic monomers of the second polymer comprise at least one acidic group, the ethylenic monomers of the second polymer comprising the at least one acidic group comprise one or more of acrylic acid, methacrylic acid, 2-ethylacrylic acid, 2-propylacrylic acid, acryloxypropionic acid, isocrotonic acid, maleic anhydride, maleic acid and half esters, half amides and half thioesters of maleic acid, fumaric acid, itaconic acid, and any combination thereof.

19. The coating composition of claim 10, wherein the acrylates or acrylamides of the second polymer comprise acrylamide, N-(2-hydroxyethyl)acrylamide, 2-hydroxyethyl methacrylate, 2-hydroxypropyl acrylate, 2-hydroxypropyl methacrylate, N-(2-hydroxyethyl) methacrylamide, N-acryloylamido-ethoxyethanol, N-(hydroxymethyl) acrylamide, N-[tris(hydroxymethyl)methyl]acrylamide, 4-hydroxybutyl acrylate, hydroxypropyl acrylate, methyl 3-hydroxy-2-methylenebutyrate, hydroxypropyl methacrylate, 2-allyloxyethanol, 3-allyloxy-1,2-propanediol, 1,4-butanediol vinyl ether, di(ethylene glycol)vinyl ether, ethylene glycol vinyl ether, N,N-1,2-dihydroxyethylene-bis-acrylamide, N,N-1,2-dihydroxyethylene-bis-methyacrylamide, N-hydroxymethyl methacrylamide, N-tri(hydroxymethyl)-methyl-methacrylamide, and any mixture of the foregoing.

* * * * *